United States Patent
Donitzky et al.

(10) Patent No.: US 8,425,499 B2
(45) Date of Patent: Apr. 23, 2013

(54) APPARATUS FOR CUTTING A HUMAN CORNEA

(75) Inventors: Christof Donitzky, Eckental/Eschenau (DE); Mathias Woelfel, Erlangen (DE)

(73) Assignee: Wavelight AG, Erlangen (DE)

( * ) Notice: Subject to any disclaimer, the term of this patent is extended or adjusted under 35 U.S.C. 154(b) by 566 days.

(21) Appl. No.: 12/692,301

(22) Filed: Jan. 22, 2010

(65) Prior Publication Data

US 2011/0184394 A1  Jul. 28, 2011

(51) Int. Cl.
*A61F 9/008* (2006.01)

(52) U.S. Cl.
USPC ............................................. 606/5; 128/898

(58) Field of Classification Search ....... 606/5; 128/898
See application file for complete search history.

(56) References Cited

U.S. PATENT DOCUMENTS

| | | | |
|---|---|---|---|
| 5,549,632 A * | 8/1996 | Lai | 606/5 |
| 5,741,245 A * | 4/1998 | Cozean et al. | 606/5 |
| 6,027,494 A * | 2/2000 | Frey | 606/5 |
| 6,110,166 A * | 8/2000 | Juhasz | 606/5 |
| 6,344,040 B1 * | 2/2002 | Juhasz et al. | 606/4 |
| 2003/0208191 A1 * | 11/2003 | Shimmel et al. | 606/5 |
| 2003/0212387 A1 * | 11/2003 | Kurtz et al. | 606/4 |
| 2004/0243111 A1 | 12/2004 | Bendett et al. | |
| 2008/0319428 A1 | 12/2008 | Wiechmann et al. | |

FOREIGN PATENT DOCUMENTS

| | | |
|---|---|---|
| EP | 1034757 | 9/2000 |
| WO | WO 2009/152838 | 12/2009 |

OTHER PUBLICATIONS

European Patent Office, International Search Report, Application No. PCT/EP2010/000393, 13 pages.

* cited by examiner

*Primary Examiner* — Henry M Johnson, III
*Assistant Examiner* — John R Downey
(74) *Attorney, Agent, or Firm* — Haynes and Boone, LLP

(57) ABSTRACT

A device for machining the human cornea with focused pulsed femtosecond laser radiation comprises scanner components for local setting of the beam focus, a control computer for controlling the scanner components, and a control program for the control computer. The control program contains instructions that upon execution by the control computer are designed to bring about the generation of an incision figure in the cornea encompassing a flap incision (38, 40). In accordance with the invention the incision figure further encompasses an auxiliary incision (50) connected with the flap incision and leading locally, preferentially directly, away from the latter as far as the surface of the cornea. The auxiliary incision is expediently generated temporally ahead of the flap incision and forms a discharge channel through which gases can escape that may arise in the course of the cutting of the flap incision.

23 Claims, 4 Drawing Sheets

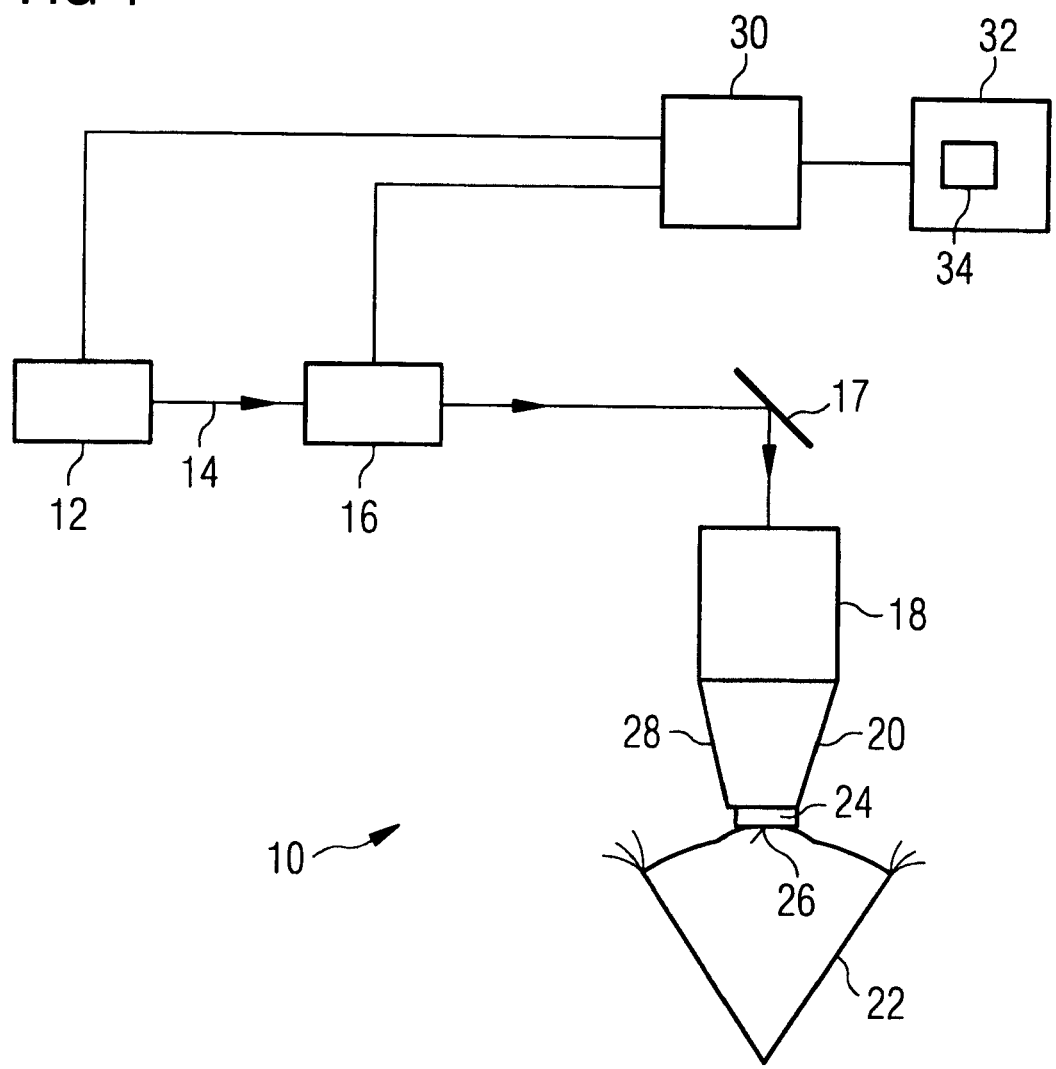

APPARATUS FOR CUTTING A HUMAN CORNEA

TECHNICAL FIELD

The invention is concerned with the generation of incisions in the human cornea by means of focused laser radiation. In particular, the invention is concerned with the preparation of a LASIK flap by means of such laser radiation.

BACKGROUND

A frequently employed technique for eliminating visual defects of the human eye—such as, for example, myopia or hyperopia or astigmatism—is so-called LASIK. LASIK stands for laser in-situ keratomileusis and designates a technique in which firstly a small cover disc in the cornea is cut free which is folded aside in order to expose the underlying tissue regions of the cornea. These exposed tissue regions are then treated in ablating manner by means of focused UV laser radiation—i.e. corneal material is removed in accordance with an ablation profile ascertained individually for the patient. The small cover disc is usually designated in specialist circles as a flap and is not severed completely from the remaining tissue of the cornea but is still connected to the rest of corneal tissue in a hinge region which in specialist circles is generally designated as a hinge. This enables a simple folding-away of the flap and, above all, a simple folding-back of the flap after the ablation. On account of the removal of material, a changed shape of the anterior surface of the cornea arises after the flap has been folded back. The associated result of this is a different refractive behaviour of the cornea and consequently of the overall system constituted by the eye. By suitable definition of the ablation profile it can be ensured that the visual defect is at least distinctly attenuated and, at best, is almost completely eliminated.

Various procedures for the preparation of the flap are known in the state of the art. One procedure uses a mechanical microkeratome—i.e. a microsurgical scalpel which cuts into the cornea with a cutting blade which is ordinarily driven in oscillating manner. Another procedure, which will be considered in more detail within the scope of the invention, uses focused short-pulse laser radiation for the purpose of preparing the flap. In this case, laser radiation with pulse durations within the femtosecond range, for example within the low three-digit femtosecond range, is ordinarily employed. In addition, the laser radiation usually has a wavelength above about 300 nm, in order to enable a coupling of the radiant energy deep into the corneal tissue. LASIK treatments in which the flap is prepared by means of such short-pulse laser radiation are often designated as fs LASIK.

For the generation of incisions by means of focused laser radiation in transparent material (transparent to the laser radiation), the so-called laser-induced optical breakthrough is utilised as a physical effect. This breakthrough ultimately results in a photodisruption of the irradiated tissue in the region of the focus. The laser radiation that is beamed in brings about a local vaporisation of the irradiated material at the focal point. In the process, gases arise which—to the extent that they are not conducted away to the outside—collect in internal cavities or are absorbed by the adjoining material. It has been found that in the course of LASIK treatments of the human eye a residence in the cornea of the gases arising in the course of preparation of the flap can lead to problems in the course of the subsequent laser ablation. In particular, it has been found that these gases can render difficult a precise tracking of the eye by means of an eye-tracker. Laser systems that are employed for the ablation of corneal tissue frequently possess such an eye-tracker, in order to register eye movements during the laser treatment and to reposition the laser radiation correspondingly. As a rule, the eye-trackers are constructed from a camera and suitable image-evaluation software which evaluates the images recorded by the camera and detects changes in the position of the eye. Frequently the image-evaluation software evaluates characteristic features of the eye—for instance, defined points of the iris or/and the pupillary centre or/and the corneal apex or/and the limbus. It has been shown that accumulations of gas remaining in the cornea, which have arisen in the course of preparation of the flap, can impede the acquisition of such characteristic features of the eye. It goes without saying that for the success of the operation a precise functioning of the eye-tracker is absolutely essential.

SUMMARY

The object of the invention is to demonstrate a way in which, in the case of LASIK treatments, an impairment of the success of the operation by troublesome accumulations of gas which arise in the course of a preparation of the LASIK flap by laser can be avoided.

With a view to achieving this object, the invention proposes a device for cutting the human cornea with focused pulsed laser radiation. The device includes controllable components for local setting of the beam focus, a control computer for controlling these components, and a control program for the control computer. The control program contains instructions that upon execution by the control computer are designed to bring about the generation of an incision figure in the cornea encompassing the flap incision, whereby according to the invention the incision figure further encompasses an auxiliary incision connected with the flap incision and leading locally as far as the surface of the cornea. The auxiliary incision establishes a connection between the flap incision and the surface of the cornea. In this way, gases arising surgically are able to escape to the surface of the cornea and hence out of the corneal tissue. A penetration of these gases into critical tissue regions of the eye can be avoided in this way. Any impairments of an eye-tracker can also be avoided better in the course of the following laser ablation.

The above reference to a local progression of the auxiliary incision is intended to serve to avoid confusions with the temporal progression in the course of generation of the auxiliary incision. A statement about a defined local progression of an incision or of a part of an incision is not intended here generally to imply any assertion whatsoever about the temporal sequence in the course of generation of the incision. Accordingly, an incision for which the assertion is made that it proceeds locally from a defined first location to a defined second location may easily be generated temporally in the direction from the second location to the first location.

In a preferred configuration the auxiliary incision begins locally directly from the flap incision and proceeds locally away from the latter as far as the surface of the cornea. Though it is also conceivable that one or more gas pockets or gas cavities within the corneal tissue adjoining the first incision are firstly generated surgically, and that the auxiliary incision leads from these gas pockets or gas cavities locally to the surface of the cornea.

The auxiliary incision preferably forms a planar and, if desired, substantially flat channel, in which connection the length, width and gradient angle of the channel can be chosen variably. The channel may have substantially constant width over its length; though generating a channel of varying width is not to be excluded. For the generation of the auxiliary incision, it may be sufficient to produce photodisruptions alongside one another in a single plane only. Though producing such photodisruptions also in two or more planes above one another is not to be excluded if a larger cross-section of the channel is desired.

In a preferred configuration the auxiliary incision is connected with the flap incision in a hinge region of the flap formed by the flap incision, and extends on the other side of the flap locally to the surface of the cornea. If desired, in this case the auxiliary incision is narrower than the hinge region.

For an optimal removal of photodisruption gases arising (i.e. gases that arise in the course of and as a consequence of the photodisruption), it is advisable that the auxiliary incision has greatest corneal depth in a region in which it is connected with the flap incision, and proceeds locally, beginning from this region, with increasingly smaller corneal depth as far as the surface of the cornea.

It is favourable if the instructions of the control program are designed to generate the auxiliary incision before the flap incision is produced. This creates the prerequisite for a gas-removal channel to be available right from the start, via which the photodisruption gases arising in the course of preparation of the flap can be conducted away.

In advantageous manner the instructions of the control program are designed to generate at least a predominant part and preferably the largest part of the auxiliary incision in a direction from the surface of the cornea to the flap incision. The formation of photodisruption gases has to be reckoned with also in the course of generation of the auxiliary incision. Insofar as the auxiliary incision is generated in the direction away from the surface of the cornea, it is possible to conduct these photodisruption gases away optimally. For example, the instructions of the control program may be designed to generate at least a predominant part of the auxiliary incision with line scans of the beam focus that progress, line by line, along a direction of extension of the auxiliary incision that proceeds from the surface of the cornea to the flap incision. Though it is just as possible that the instructions of the control program are designed to generate at least a predominant part of the auxiliary incision with line scans of the beam focus that progress, line by line, transverse to a direction of extension of the auxiliary incision that proceeds from the surface of the cornea to the flap incision.

The flap incision may encompass a bed incision completely situated deep within the corneal material, preferentially at substantially constant depth, as well as a lateral incision adjoining the bed incision and guided out locally to the surface of the cornea. The bed incision is so designated because it defines the stromal bed for the flap. Given prior applanation (levelling) of the surface of the cornea by abutment against a suitable applanation face, the bed incision may be realised, for example, by a flat surface incision which is inserted at constant depth of the cornea. In principle, it is conceivable to generate the bed incision with line scans or with spiral scans of the radiation focus. However, for an optimal removal of the photodisruption gases arising in the course of generation of the bed incision it is proposed that the instructions of the control program are designed to generate the bed incision with line scans of the radiation focus that progress increasingly, line by line, in the direction away from a hinge region of the flap. At the same time, the instructions of the control program are expediently designed to generate the lateral incision temporally after the bed incision. Since the lateral incision leads locally out to the surface of the cornea, it is advisable to generate the lateral incision, beginning from its most low-lying regions, in a direction towards the surface of the cornea. Of course, an opposite direction in the course of generation of the lateral incision is equally conceivable.

For a good transition, sufficiently permeable to the photodisruption gases, between the auxiliary incision and the flap incision, it is advisable that the instructions of the control program are designed to bring about, in a transition region between auxiliary incision and flap incision, line scans of the beam focus that progress, line by line, transverse to the transition direction. Equally, for a good opening of the auxiliary incision outwards, it is advisable that the instructions of the control program are designed to bring about, in the surface-side end region of the auxiliary incision (by 'end region' here a local end region is meant; the surface-side end region may perfectly well be the starting region in connection with the generation of the auxiliary incision), line scans of the radiation focus that progress, line by line, transverse to the direction of entry of the auxiliary incision into the cornea.

In a further development of the invention the device may further include a contact element that is transparent to the laser radiation, with a contact face intended for abutment against the eye, the instructions of the control program being designed to generate the auxiliary incision in such a way that its end opening out on the surface of the cornea lies in a region of the cornea in which the latter bears against the contact face of the contact element.

In a first configuration the contact face may exhibit a plane surface portion for levelling a part of the surface of the cornea, the instructions of the control program being designed to generate the auxiliary incision in such a way that its end opening out on the surface of the cornea lies in a region of the cornea in which the latter bears against the plane surface portion of the contact face.

In an alternative configuration the contact face may exhibit a plane surface portion for levelling a part of the surface of the cornea, as well as a surface portion adjoining the plane surface portion and proceeding obliquely relative to the latter in the direction towards the side of the contact element facing away from the eye, the instructions of the control program being designed to generate the auxiliary incision in such a way that its end opening out on the surface of the cornea lies in a region of the cornea in which the latter bears against the obliquely proceeding surface portion of the contact face. The obliquely proceeding surface portion is preferentially of rounded construction and adjoins the plane surface portion in kink-free manner.

According to another further embodiment the device may include a contact element that is transparent to the laser radiation, with a contact face intended for abutment against the eye, the instructions of the control program being designed to generate the auxiliary incision in such a way that its end opening out on the surface of the cornea lies outside a region of the cornea in which the latter bears against the contact face of the contact element.

In this further embodiment, for the purpose of adapting the refractive index a chamber is preferentially provided on the side of the contact element facing towards the eye, which via a filling-channel arrangement is capable of being filled with a liquid or with another suitable flowable medium which reduces the jump in refractive index from the contact element to the cornea and expediently possesses optically homogeneous properties. Instead of being present in liquid form, this medium may also be present, for example, in gel-like form. Also not excluded is the use of a gaseous medium. The instructions of the control program are in this case designed to generate the auxiliary incision in such a way that it leads into the liquid-filled chamber (or, generally, into the chamber filled with the medium).

In the case of formation of the flap incision with a flat bed incision, the instructions of the control program are preferentially designed to generate the auxiliary incision opening out into the chamber and the bed incision in a common plane. This relates to the flattened case—that is to say, the state in which the eye is bearing against the contact element.

A process for treating the human eye includes the following steps: providing first pulsed laser radiation, the laser radiation having a radiation focus, directing the first laser radiation onto a human cornea to be treated, controlling the radiation focus of the first laser radiation for the purpose of generating a flap incision in the cornea forming a flap, as well as an auxiliary incision connected with the flap incision and leading locally as far as the surface of the cornea.

The process may further include the following steps: folding the flap away, in order thereby to expose underlying corneal tissue, providing second pulsed laser radiation, directing the second laser radiation onto the exposed corneal tissue, and ablating the exposed corneal tissue with the second laser radiation in accordance with a predetermined ablation profile.

The first laser radiation preferentially has pulse durations within the femtosecond range and has a wavelength above 300 nm. The second laser radiation has a wavelength within the UV range and may, for example, be generated by an excimer laser, for instance by an ArF excimer laser radiating at 193 nm.

BRIEF DESCRIPTION OF THE DRAWINGS

The invention will be elucidated further in the following on the basis of the appended drawings. Represented are:

FIG. 1 in schematic block representation, an exemplary embodiment of a laser arrangement for inserting intracorneal incisions, FIGS. 2a and 2b two variants of a corneal incision figure for preparing a LASIK flap, FIG. 3 the incision figure shown in FIG. 2a, in a cross-sectional view, FIG. 4 an exemplary scan pattern of a laser beam that is used for generating the incision figure shown in FIG. 2a, FIGS. 5 and 6 two variants for generating a flap incision, supplemented by an auxiliary incision, in a flattened cornea.

DETAILED DESCRIPTION

Figure 2A:
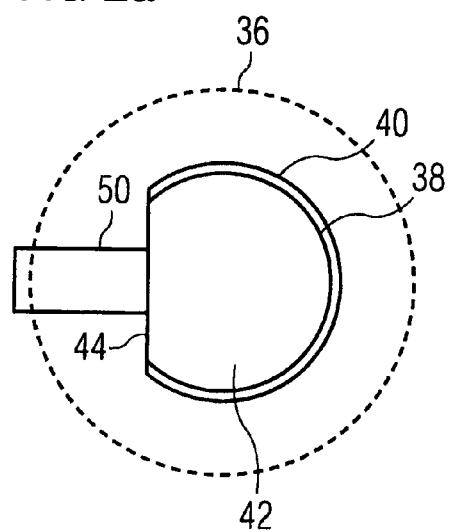

The laser arrangement shown in FIG. 1—denoted generally by 10—includes a laser source 12 which generates a laser beam 14 with pulse durations within the femtosecond range. In the beam path of the laser beam 14 a series of components are arranged, inter alia a scanner 16, indicated here schematically as a unitary functional block, an immovable deflecting mirror 17 and also a focusing objective 18. The scanner 16 serves for transverse and longitudinal local control of the focal point of the laser beam 14. 'Transverse' here designates a direction at right angles to the direction of propagation of the laser beam 14; 'longitudinal' corresponds to the direction of beam propagation. In conventional notation the transverse plane is designated as the x-y plane, whereas the longitudinal direction is designated as the z-direction. For the purpose of transverse deflection of the laser beam 14 (i.e. in the x-y plane) the scanner 16 may, for example, include a pair of galvanometrically actuated scanner mirrors which are capable of being tilted about mutually perpendicular axes. Alternatively, for example, a transverse deflection by means of an electro-optical crystal is conceivable. For the z-control of the position of the focus the scanner 16 may contain, for example, a longitudinally adjustable lens or a lens of variable refractive power or a deformable mirror, with which the divergence of the laser beam 14 and consequently the z-position of the beam focus can be influenced. It will be understood that the components of the scanner 16 serving for the transverse focus control and for the longitudinal focus control may be arranged distributed along the beam path of the laser beam 14 and, in particular, apportioned to different modular units. For example, the function of the z-focus control may be fulfilled by a lens arranged in beam-expanding optics (beam expander, e.g. Galilean telescope), whereas the components serving for the transverse focus control may be accommodated in a separate modular unit between the beam-expanding optics and the focusing objective 18. The representation of the scanner 16 as a unitary functional block in FIG. 1 serves merely for better clarity of layout.

The focusing objective 18 is preferably an f-theta objective and is preferentially separably coupled on its beam-emergence side with a patient adapter 20 which forms an abutment interface for the cornea of an eye 22 to be treated. For this purpose the patient adapter 20 exhibits a contact element 24 that is transparent to the laser radiation and that on its underside facing towards the eye exhibits a abutment face (contact face) 26 for the cornea. In the exemplary case that is shown, the abutment face 26 is constructed as a plane face and serves for levelling the cornea, by the contact element 24 being pressed against the eye 22 with appropriate pressure or by the cornea being aspirated onto the contact face 26 by reduced pressure. The contact element 24 (in the case of plane-parallel construction, ordinarily designated as the applanation plate) is fitted at the narrower end of a conically widening carrier sleeve 28. The connection between the contact element 24 and the carrier sleeve 28 may be inseparable, for example by virtue of adhesion, or it may be separable, for instance by virtue of a screwed joint. At its wider sleeve end the carrier sleeve 28 has, in a manner not represented in any detail, suitable coupling structures for coupling onto the focusing objective 18.

The laser source 12 and the scanner 16 are controlled by a control computer 30 which operates in accordance with a control program 34 stored in a memory 32. The control program 34 contains instructions (program code) that upon execution by the control computer 30 bring about such a local control of the beam focus of the laser beam 14 that a LASIK flap arises in the cornea of the eye 22 bearing against the contact element 24. The incision figure generated in the cornea in this regard encompasses not only a flap incision forming the actual flap but additionally an auxiliary incision, through which photodisruption gases arising are able to escape from the cornea to the outside.

Figure 2B:
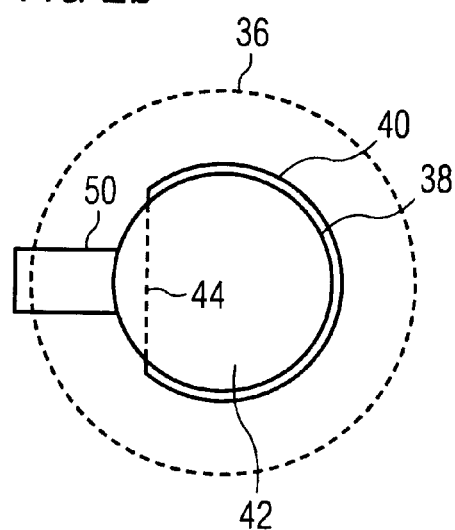

FIGS. 2a and 2b show two variants of such an incision figure. In both cases a dashed circular line 36 denotes the levelling region in which the cornea is levelled as a consequence of its abutment against the contact element 24. It will be understood that, in reality, the levelling region 36 does not have to be exactly circular. In particular, in view of the ordinarily differing radii of curvature in the principal meridional directions of the surface of the cornea an outline of the levelling region 36 deviating from a circular shape may arise.

In the exemplary cases that are shown, the flap incision forming the flap is composed of two partial incisions. A first partial incision is a so-called bed incision, which severs the flap from the stromal bed and is realised as a flat surface incision parallel to the contact face 26. The bed incision is denoted by 38 in FIGS. 2a and 2b. Said bed incision is produced at a depth of the cornea corresponding to the desired thickness of the flap. Whereas in FIG. 2b it extends over a complete circular area, in FIG. 2a it is shortened by a segment of a circle and terminates at a chord of a circle. It will be understood that, depending on the desired shape of the flap, the bed incision 38 may have a non-circular outline, for example an elliptical outline. In any case, the bed incision 38 is complemented by a lateral incision 40 which proceeds along a partial periphery of the bed incision 38 and—considered locally—extends to the surface of the cornea, beginning from the bed incision 38. The lateral incision 38 is also generated in the levelled state of the cornea, i.e. with the eye 22 bearing against the contact face 26, and proceeds obliquely outwards locally from the bed incision 38. Alternatively, the lateral incision 40 may proceed obliquely inwards locally from the bed incision 38.

The flap is formed by the bed incision 38 and the lateral incision 40 together. Said flap is denoted by 42 in FIGS. 2a and 2b and also in FIG. 3. In the part of the periphery of the bed incision 38 not encompassed by the lateral incision 40 the flap 42 is still connected to the remaining corneal tissue (apart from the region of an auxiliary incision yet to be elucidated). The transition region between the flap 42 and the remaining corneal tissue forms a hinge which permits the flap to be folded away in order to expose the underling tissue for an ablating laser treatment. The hinge line is, at least in sufficient approximation, rectilinear and is denoted by 44 in FIGS. 2a and 2b. In the case of FIG. 2a, it is situated approximately overlapping the straight edge of a segment of a circle at which the bed incision 38 terminates; in FIG. 2b it proceeds, at least when considered in the top view of this Figure—transversely beyond the bed incision 38 from one peripheral end of the lateral incision 40 to the other.

Figure 3:
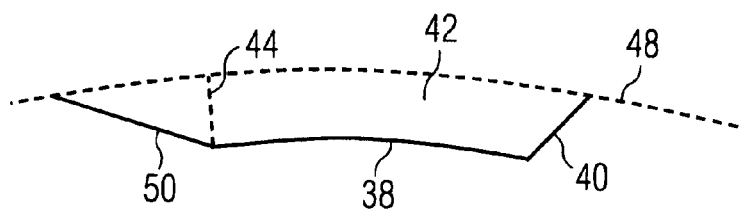

FIG. 3 illustrates the two partial incisions (bed incision, lateral incision) of the flap 42 for the case of FIG. 2a with the cornea relaxed, i.e. after removal of the eye 22 from the contact element 24. The curved line 48 which has been drawn with dashes designates the anterior surface of the cornea.

As a consequence of the vaporisation of corneal tissue in the course of the cutting of the flap 42, gases arise which are able to diffuse out of the cut surface into the adjoining tissue regions. The residence of such gases in the eye may, on the one hand, be dangerous if the gases penetrate into particularly sensitive regions of the eye; on the other hand, it may impair the functionality of an eye-tracker in the course of the subsequent laser ablation of the stromal bed. Therefore the incision figure generated in the cornea is not only limited to the flap incision but exhibits an additional auxiliary incision 50 which enables an escape from the eye of the gases arising in the course of preparation of the flap. In the exemplary cases of FIGS. 2a, 2b which are shown, the auxiliary incision 50 directly adjoins the bed incision 38, to be specific in the hinge region of the flap 42—that is to say, where the lateral incision 40 leaves free a part of the periphery of the bed incision 38. Starting from the bed incision 38, the auxiliary incision 50 extends locally away from the flap 42 in the direction towards the corneal surface 48, i.e. it proceeds on the other side of the flap 42. In this case the auxiliary incision 50 proceeds locally at increasingly smaller depth within the cornea; in particular, it ascends steadily to higher corneal layers until it reaches the surface of the cornea. In this way it forms a channel (tunnel), by which the bed incision 38 is connected with the environment outside the eye, so that gases that arise in the course of the cutting of the bed incision 38 are able to escape outwards through the channel.

As can be discerned in FIGS. 2a, 2b, in the exemplary cases that are shown the channel formed by the auxiliary incision 50 has a constant width over its length, being narrower than the hinge region of the flap 42 and, relative to the direction of the hinge axis 44, situated approximately centrally in the hinge region. It will be understood that the auxiliary incision 50 may also be as wide as the hinge region or even wider than the latter. Restrictions in this regard are not intended within the scope of the invention.

In FIG. 3 the auxiliary incision 50 is represented as a rectilinear incision. It will be understood that the auxiliary incision 50 may alternatively rise in a curved path locally from the bed incision 38 to the surface of the cornea. The intensity of the ascent of the auxiliary incision 50 may also be defined differently. Comparable remarks apply to the width of the auxiliary incision 50; said width may vary over the length of the auxiliary channel; for example, it may become larger in the direction towards the surface of the cornea.

The point at which the auxiliary incision 50 reaches the surface of the cornea may lie outside the levelling region 36 of the cornea, as indicated in FIGS. 2a, 2b where the auxiliary incision 50 extends outwards beyond the levelling region 36. Nevertheless, it is just as possible that the auxiliary incision 50 is guided locally up to the surface of the cornea within the levelling region 36 or at the edge of the levelling region.

Figure 4:
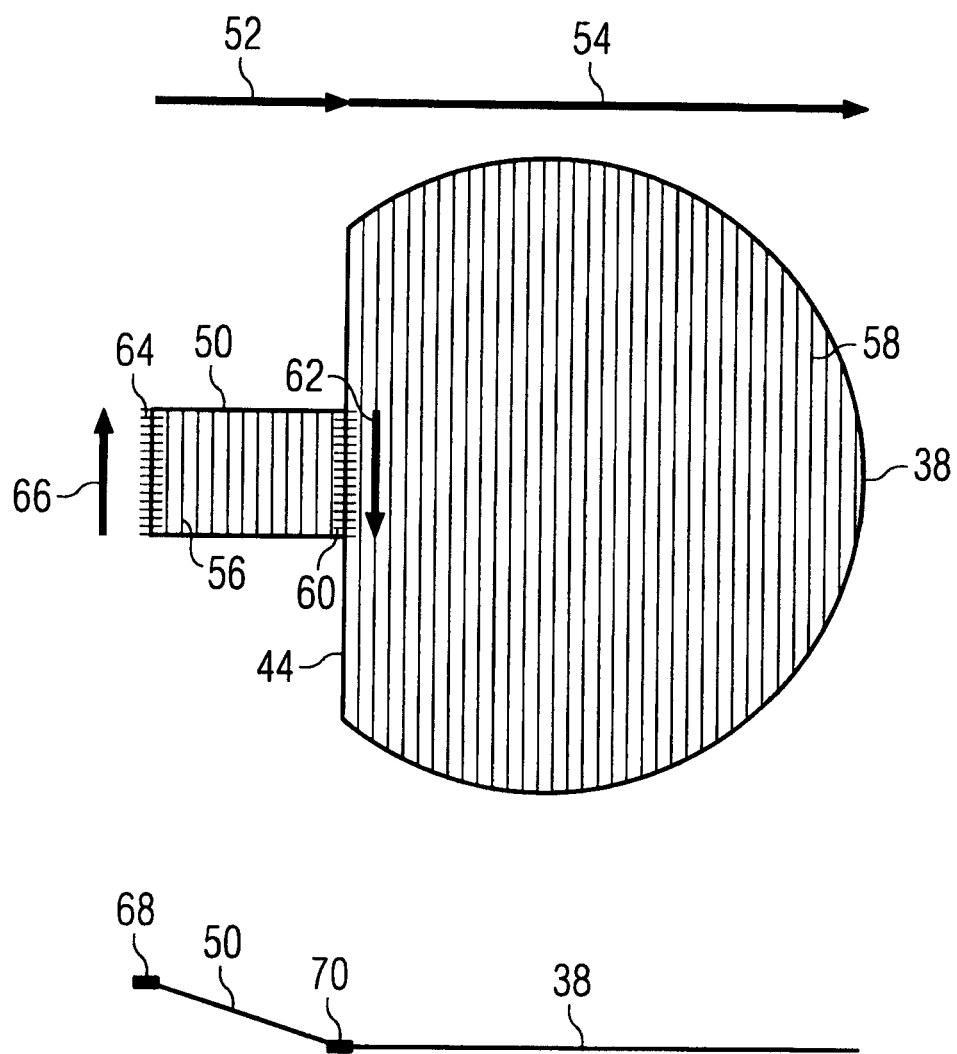

For the purpose of elucidating the temporal sequence in which the auxiliary incision 50 and the bed incision 38 are inserted, and the scan patterns that are used in the process for the laser beam 14, reference will now additionally be made to FIG. 4. The bed incision 38 and the auxiliary incision 50 are shown therein; the lateral incision 40 has been omitted for the sake of clarity of layout; it is usually generated only after the bed incision 38, to be specific starting from the bed incision 38 in the direction towards the surface of the cornea.

The auxiliary incision 50, on the other hand, is generated before the bed incision 38 is inserted. This guarantees that gases are able to escape outwards via the auxiliary incision 50 already at the start of the preparation of the bed incision 38. The auxiliary incision 50 is generated from the surface of the cornea—that is to say, in the direction towards deeper corneal layers. This is indicated by an arrow 52 which has been drawn at the top in FIG. 4. After generation of the auxiliary incision 50, the bed incision 38 is generated, to be specific beginning in the hinge region 44—that is to say, where the auxiliary incision 50 terminates. Beginning from the hinge region 44, the bed incision 38 is gradually generated in the direction towards the end that is remote from the hinge. This direction of generation of the bed incision 38 is indicated at the top in FIG. 4 by an arrow 54.

On its largest part the auxiliary incision 50 is generated by line scans of the laser beam 14 that follow one another, line by line, in the arrow direction 52, i.e. in the direction from the surface of the cornea towards the bed incision 38. The individual scan lines of this line scan are denoted by 56. The bed incision 38 is also generated with a scan pattern consisting of line scans, the individual scan lines following one another in the direction from the hinge region 44 towards the end of the bed incision 38 that is remote from the hinge, i.e. in the arrow direction 54. The scan lines of the bed incision 38 are denoted by 58 in FIG. 4.

Whereas the representation shown in FIG. 4 is an example of a succession of the scan lines 56 in the direction of the longitudinal extent of the auxiliary incision 50 ('longitudinal extent' in this connection means an extent from the surface of the cornea to the flap incision, more precisely to the bed incision), it is readily conceivable to generate the main part of the auxiliary incision 50 with a line scan, the scan lines of which follow one another at right angles to the longitudinal extent of the auxiliary incision. The scan lines of such a transverse scan then proceed similarly to the scan lines 60 and 64.

The transition region between the auxiliary incision 50 and the bed incision 38 is, in addition, prepared with line scans that progress, line by line, at right angles to the transition direction. 'Transition direction' here means the direction in which the auxiliary incision 50 merges with the bed incision 38. This direction corresponds to the direction of the arrows 52, 54. By producing scan lines alongside one another at right angles to this direction in the transition region, it is possible to realise a good connection, open for the passage of gas, between the auxiliary incision 50 and the bed incision 38. The transverse scan lines that have been produced in the transition region are denoted by 60 in FIG. 4. The direction of their succession is represented by an arrow 62 (may optionally also be in the opposite arrow direction).

Similar transverse scan lines are, furthermore, produced in the entry region of the auxiliary incision 50—that is to say, where it enters the corneal tissue on the surface of the cornea. The corresponding scan lines are denoted by 64 in FIG. 4; the direction of their succession is indicated by an arrow 66 (may optionally also be in the opposite arrow direction). These scan lines 64 proceeding at right angles to the entry direction of the auxiliary incision are expedient in order to create a clean opening of the auxiliary incision 50 on the surface of the cornea.

As far as the temporal sequence is concerned, expediently firstly the scan lines 64 are produced, subsequently the scan lines 56, thereupon the scan lines 60 and, thereafter, the scan lines 58. In this manner the generation of the incisions progresses increasingly from the surface in the direction towards deeper layers. The representation in the lower part of FIG. 4 illustrates this once again. Therein the auxiliary incision 50, the bed incision 38 and also the entry region (denoted by 68) and the transition region between the two incisions (denoted by 70) are shown in a view from the side. With the temporal sequence of the scan lines that has been elucidated it is possible that during the generation of the auxiliary incision 50 and also during the generation of the bed incision 38 a tunnel to the outside is already always open, through which gases currently arising are able to escape.

In a modification of the above sequence, the generation of the transition region 70 may be temporally favoured and may be undertaken ahead of the entry region 68. After this, as previously, the remainder (i.e. the main part) of the auxiliary incision 50 and also the bed incision 38 are inserted. In a further modification, firstly the transition region 70 may be generated. Then the main part of the auxiliary incision 50 and, after this, the entry region 68 are generated. After complete generation of the auxiliary incision 50, the bed incision 38 is inserted. Though it should be pointed out that within the scope of the invention no restriction whatsoever to a defined temporal sequence of the generation of the incisions is intended.

In principle, in the entire auxiliary incision 50 (including the entry region 68 and the transition region 70) and also in the bed incision 38 the local spacings of the photodisruptions following one another along the scan lines may be substantially the same. The same applies to the mutual spacing of consecutive scan lines.

However, it is possible to vary the local spacing of the photodisruptions or/and the mutual line spacing at least in parts of the auxiliary incision 50 or/and of the bed incision 38. In particular, it is conceivable to choose for the entry region 68 or/and for the transition region 70 a closer local succession of the photodisruptions or/and to choose a closer mutual spacing of the consecutive scan lines than for the main part of the auxiliary incision 50 and for the bed incision 38.

The position of the auxiliary incision 50 described here relative to the bed incision 38 guarantees that the two incisions do not overlap reciprocally. This is because no further underlying plane can be cut through an already cut plane. Since in the ideal case the auxiliary incision 50 should already be present when the cutting of the bed incision 38 is begun, it is advisable to cut the auxiliary incision 50 into the cornea from outside the flap (further remote from the corneal centre) and to allow it to merge with the bed incision in the hinge region of the flap.

Figure 5:
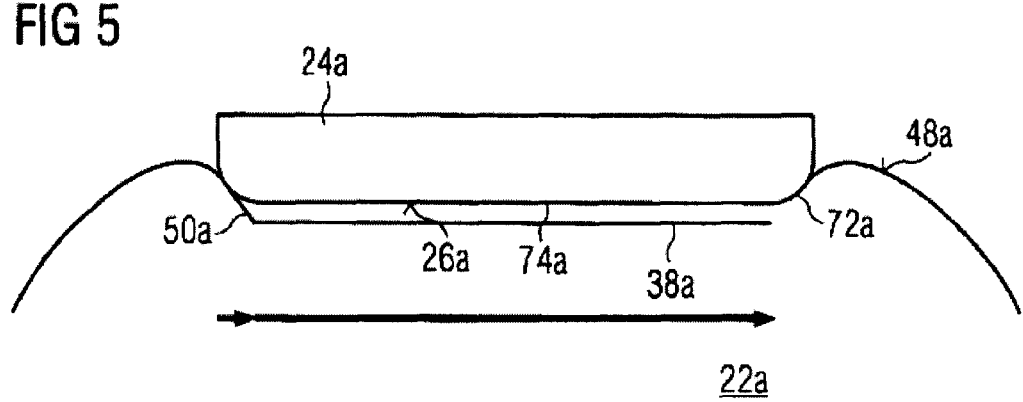
Figure 6:
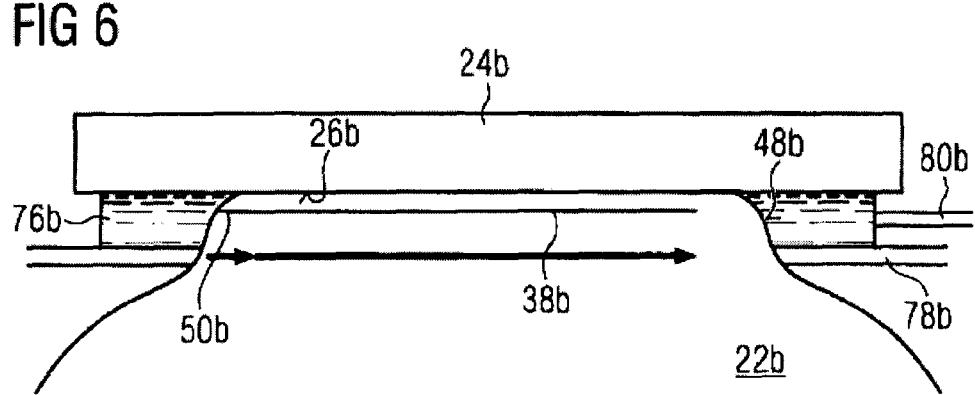

In FIGS. 5 and 6, identical or identically-acting elements are denoted by the same reference symbols as in the preceding Figures, but supplemented by a lower-case letter. To the extent that nothing else results in the following, reference is made to what was stated above for the purpose of elucidating these elements.

It has already been explained that the auxiliary incision may open out to the surface of the eye inside or outside the levelled region of the cornea. This assertion may be generalised to the extent that the auxiliary incision may open out to the surface of the cornea at a point that lies inside or outside (or at the edge of) a region in which the cornea bears against the contact element of the patient adapter. Even though within the scope of the invention a very extensive levelling of the surface of the cornea by the contact element is striven for, it is nevertheless not necessary that the cornea bears against the contact face exclusively in flat regions of said contact face.

In this regard, reference will now be made to the variant shown in FIG. 5. Therein a contact element 24a is shown which on its underside facing towards the eye bears a contact face 26a which in its main part is of flat construction but in its marginal region is rounded and proceeds there obliquely to the flat main part in the direction away from the eye 22a. The rounded surface portion forms a ring segment surrounding the flat main part of the contact face 26 and is denoted by 72a. The flat main part of the contact face 26a, on the other hand, is denoted by 74a. The contact between the contact element 24a and the eye 22a is established in such a way that the cornea rests closely against the contact face 26a not only in the main part 74a but also in the outer ring segment 72a.

The auxiliary incision 50a is generated in such a way that it emerges to the surface of the cornea in the region of the ring segment 72a (the term 'emerge' is meant here purely locally and implies no statement whatsoever about the temporal sequence in which the individual parts of the auxiliary incision are prepared). This means the auxiliary incision 50a opens out at a point on the surface of the cornea where the cornea bears against the rounded ring segment 72a. This is favourable to the extent that any possible gases which arise in the course of preparation of the auxiliary incision 50a and of the bed incision 38a and escape to the outside though the auxiliary incision 50a can, at least for the most part, reach the surrounding air and are not drawn deeper between the contact element 24a and the corneal surface 48a by capillary action. In other words, a better degassing of the operative field is possible in this way.

The rounded ring segment 72a adjoins the flat main part 74a of the contact face 26a preferentially in kink-free manner. Nevertheless, it is not to be excluded in principle to construct the ring segment 72a, instead of with a roundish configuration, in the form of a rectilinear oblique surface which is separated from the flat main part 74a by a kink.

The variant shown in FIG. 6 illustrates an example in which the auxiliary incision 50b opens out at a point on the surface of the cornea where the cornea does not bear against the contact face 26b of the contact element 24b. Instead, it opens out outside the flattened region of the corneal surface 48b. In concrete terms, in the exemplary case shown in FIG. 6 the auxiliary incision 50 opens out into an annular chamber 76b which is delimited between the contact element 24b, the corneal surface 48b and a sealing component 78b which, for example, may be part of a suction ring (not represented in any detail) to be attached onto the eye 22b. Represented schematically in FIG. 6 is a filling channel 80b, via which the annular chamber 76b is capable of being filled with a physiological liquid (e.g. solution of common salt). The filling channel 80b may be part of the aforementioned suction ring.

The bed incision 38b and the auxiliary incision 50b may in this variant be generated in a common plane, i.e. with constant z-position of the beam focus of the laser radiation that is used for the generation of the incisions. The direction of generation corresponds to that shown in FIG. 4, i.e. the auxiliary incision 50b is generated before the bed incision 38b, to be specific expediently in a direction from the surface of the cornea to the bed incision 38b.

The invention claimed is:

1. Process for treating the human eye, including:
providing first pulsed laser radiation, the laser radiation having a radiation focus;
directing the first laser radiation onto a human cornea of an eye to be treated; and
controlling the radiation focus of the first laser radiation for the purpose of generating a flap incision in the cornea forming a flap and also for the purpose of generating an auxiliary incision connected with the flap incision,
wherein the flap incision includes a bed incision and a lateral incision, the bed incision being a flat surface incision in a stromal bed of the eye and the lateral incision extending from the bed incision to a surface of the cornea to define the flap, the flap connected to the stromal bed by a hinge defined by remaining corneal tissue;
wherein the auxiliary incision is formed temporally before the flap incision, the auxiliary incision extending from a surface of the cornea to a depth of the bed incision such that the auxiliary incision defines a channel having a substantially constant width and gradient angle along its length such that gases formed subsequently during at least the bed incision are able to escape from the eye;
wherein the auxiliary incision extends from the surface of the cornea on a first side of the hinge and the lateral incision of the flap incision extends from the surface of the cornea on a second side of the hinge opposite the first side.

2. Process according to claim 1, further including:
folding the flap away, in order thereby to expose underlying stromal bed;
providing second pulsed laser radiation;
directing the second laser radiation onto the stromal bed; and
ablating the exposed stromal bed with the second laser radiation in accordance with a predetermined ablation profile.

3. Process according to claim 1, wherein the auxiliary incision forms a planar, substantially flat channel from the flap incision to the surface of the cornea.

4. Process according to claim 3, wherein the channel has substantially constant thickness over its length.

5. Process according to claim 1, wherein the auxiliary incision is connected with the flap incision adjacent the hinge formed by the flap incision.

6. Process according to claim 1, wherein the auxiliary incision has greatest corneal depth in a region in which it is connected with the flap incision and, starting from this region, proceeds locally at increasingly smaller corneal depth to the surface of the cornea.

7. Process according to claim 1, wherein the auxiliary incision is generated beginning at the surface of the cornea and extending inward to the depth of the bed incision.

8. Process according to claim 1, wherein a majority of the auxiliary incision is generated in a direction from the surface of the cornea to the flap incision.

9. Process according to claim 1, wherein a majority of the auxiliary incision is generated with line scans of the radiation focus of the first laser radiation that progress, line by line, along a direction of extension of the auxiliary incision that proceeds from the surface of the cornea to the flap incision.

10. Process according to claim 1, wherein a majority of the auxiliary incision is generated with line scans of the radiation focus that progress, line by line, transverse to a direction of extension of the auxiliary incision that proceeds from the surface of the cornea to the flap incision.

11. Process according to claim 1, wherein the bed incision is generated temporally ahead of the lateral incision, the bed incision being generated with line scans of the radiation focus of the first laser radiation that progress increasingly, line by line, in a direction away from a transition from the auxiliary incision to the bed incision.

12. Process according to claim 1, wherein line scans of the radiation focus of the first laser radiation that progress, line by line, transverse to the transition direction are brought about in a transition region between auxiliary incision and flap incision.

13. Process according to claim 1, wherein line scans of the radiation focus of the first laser radiation that progress, line by line, transverse to a direction of entry of the auxiliary incision into the cornea are brought about in a surface-side end region of the auxiliary incision.

14. Process according to claim 1, wherein the first laser radiation has pulse durations within the femtosecond range.

15. Process according to claim 1, further including:
providing a contact element that is transparent to the first laser radiation, with a contact face;
bringing the cornea into contact with the contact face; and
generating an auxiliary incision so that its end opening out on the surface of the cornea lies in a region of the cornea in which the latter bears against the contact face.

16. Process according to claim 15, wherein the auxiliary incision is generated in such a way that its end opening out on the surface of the cornea lies in a region of the cornea in which the latter bears against a plane surface portion of the contact face.

17. Process according to claim 15, wherein the contact face exhibits a plane surface portion for levelling a part of the surface of the cornea, as well as a surface portion adjoining the plane surface portion and proceeding obliquely relative to the latter in the direction towards the side of the contact element facing away from the eye, the auxiliary incision being generated in such a way that its end opening out on the surface of the cornea lies in a region of the cornea in which the latter bears against the obliquely proceeding surface portion of the contact face.

18. Process according to claim 17, wherein the obliquely proceeding surface portion is of rounded construction and adjoins the plane surface portion in kink-free manner.

19. Process according to claim 1, further including:
providing a contact element that is transparent to the first laser radiation, with a contact face;
bringing the cornea into contact with the contact face; and generating an auxiliary incision so that its end opening out on the surface of the cornea lies outside a region of the cornea in which the surface of the cornea bears against the contact face.

20. Process according to claim 19, further including:

filling a chamber provided on a side of the contact element facing towards the eye with a flowable medium; and generating the auxiliary incision so that it leads into the chamber filled with the medium.

21. Process according to claim 20, wherein the medium is a liquid.

22. Process according to claim 21, wherein the liquid is a solution of common salt.

23. Process according to claim 19, wherein auxiliary incision is generated beginning at the surface of the cornea and extending inward to the depth of the bed incision and the bed incision is generated beginning at a transition between the auxiliary incision and the bed incision positioned adjacent to where the hinge will be defined and extending in a direction away from the auxiliary incision such that the bed incision is opposite the auxiliary incision relative to where the hinge will be defined.

* * * * *